United States Patent
Buyske et al.

(10) Patent No.: US 8,187,806 B2
(45) Date of Patent: May 29, 2012

(54) ASSOCIATION OF GSTM1 WITH AUTISM AND ASSAYS AND METHODS BASED THEREON

(75) Inventors: Steven Buyske, Princeton, NJ (US); Edward S. Stenroos, Harrison, NJ (US); William G. Johnson, Short Hills, NJ (US)

(73) Assignees: University of Medicine and Dentistry of New Jersey, Somerset, NJ (US); Rutgers, The State University of New Jersey, New Brunswick, NJ (US)

( * ) Notice: Subject to any disclaimer, the term of this patent is extended or adjusted under 35 U.S.C. 154(b) by 39 days.

(21) Appl. No.: 12/069,988

(22) Filed: Feb. 11, 2008

(65) Prior Publication Data

US 2008/0293058 A1    Nov. 27, 2008

Related U.S. Application Data

(60) Provisional application No. 60/900,513, filed on Feb. 9, 2007.

(51) Int. Cl.
*C12Q 1/68* (2006.01)
*C12P 19/34* (2006.01)

(52) U.S. Cl. .................. 435/6.1; 435/6.11; 435/6.12

(58) Field of Classification Search ................... None
See application file for complete search history.

(56) References Cited

U.S. PATENT DOCUMENTS 6,912,492 B1 *   6/2005   Johnson et al. .................. 703/2

OTHER PUBLICATIONS

James et al., "Metabolic Endophenotype and Related Genotypes are Associated With Oxidative Stress in Children With Autism," American Journal of Medical Genetics Part B, Dec. 2006, vol. 141B, pp. 947-956.*

Hsueh et al., "Genome-Wide and Fine-Mapping Linkage Studies of Type 2 Diabetes and Glucose Traits in the Older Order Amish," Diabetes, Feb. 2003, vol. 52, pp. 550-557.*

Buyske et al., "Analysis of case-parent trios at a locus with a deletion allele: association of GSTM1 with autism," BMC Genetics, 2006, vol. 7, pp. 1-9.*

* cited by examiner

*Primary Examiner* — Young J Kim
(74) *Attorney, Agent, or Firm* — Fox Rothschild LLP

(57) ABSTRACT

The present invention provides novel markers and assays for autism based on the association of GSTM1 with autism. The invention relates to the use and application of as a susceptibility marker for autism. GSTM1 may be combined with other markers in methods and assays for diagnosis, prenatal diagnosis, and assessment of autism. The invention further relates to a likelihood ratio test. In addition, the present invention discloses a novel method for identifying individuals who are genetically susceptible to have offspring with autism wherein the genotype of GSTM1, alone or in combination with other genetic markers, is determined.

10 Claims, No Drawings

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: forward primer

<400> SEQUENCE: 1
gaactccctg aaaagctaaa gc                                        22

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gttgggctca aatatacggt gg                                        22

<210> SEQ ID NO 3
<211> LENGTH: 22
<212> TYPE: DNA
<213> ORGANISM: Artificial Sequence
<220> FEATURE:
<223> OTHER INFORMATION: forward primer

<400> SEQUENCE: 3
ggacattttg gagaaccaga cc                                        22

<210> SEQ ID NO 4
<211> LENGTH: 22
<212> TYPE: DNA
<213> ORGANISM: Artificial Sequence -continued

```
<220> FEATURE:
<223> OTHER INFORMATION: reverse primer

<400> SEQUENCE: 4
ctggattgta gcagatcatg cc                                          22

<210> SEQ ID NO 5
<211> LENGTH: 17
<212> TYPE: DNA
<213> ORGANISM: Artificial Sequence
<220> FEATURE:
<223> OTHER INFORMATION: GSTM1 specific probe oligonucleotide

<400> SEQUENCE: 5
tggacaacca tatgcag                                                17
```

ASSOCIATION OF GSTM1 WITH AUTISM AND ASSAYS AND METHODS BASED THEREON

CROSS REFERENCE TO RELATED APPLICATIONS

The present application claims priority of provisional application U.S. Ser. No. 60/900,513, filed on Feb. 9, 2007, bearing the same title as the present application, the disclosure of which is incorporated by reference herein in its entirety. Applicants claim the benefits of such application under 35 U.S.C. §119(e).s

FIELD OF THE INVENTION

The present invention relates generally to markers and assays for autism and to the association of GSTM1 with autism. The invention relates to the use and application of GSTM1 as a susceptibility marker for autism. GSTM1 may be combined with other markers in methods and assays for diagnosis, prenatal diagnosis, and assessment of autism. The invention further relates to a likelihood ratio test.

BACKGROUND OF THE INVENTION

Autism (autistic disorder) is a pervasive developmental disorder with diagnostic criteria based on abnormal social interactions, language abnormalities, and stereotypes evident prior to 36 months of age [5]. Despite its lack of Mendelian transmission autism is highly genetically determined [6].

The vast majority of cases of autism are unrelated to known teratogens but the phenotypic expression of autism may be affected by the interaction of environmental factors with multiple gene loci. There is evidence supporting a role for oxidative stress in autism [7, 8]. Oxidative stress could interact with common functional polymorphic variants of genes that protect against oxidative stress and could thus affect brain development during gestation or possibly after gestation, contributing to expression of autism. Glutathione (GSH) is the most important endogenous antioxidant due to its ability to bind electrophilic substrates through its free sulfhydryl group [9] and is the most abundant non-protein thiol, occurring in millimolar concentrations in human tissues [10]. Low plasma total GSH (tGSH) levels, elevated levels of oxidized GSH (GSSG) and low ratios of tGSH:GSSG have been reported in autism [11].

Glutathione-S-transferases (GSTs), are an important class of antioxidant enzymes that catalyze conjugation of GSH to toxic electrophiles. GSTs are abundant, accounting for up to 10% of cellular protein [12]. Some genetic polymorphisms of GSTs are known to affect enzyme function. It is possible that a functional GST polymorphism could contribute to the pathogenesis of autism, an effect that could be potentiated by reduced levels of GSH, one of the substrates of GSTs. GSTs are Phase II enzymes that conjugate GSH to activated toxins, xenobiotics and metabolites including products of Phase I enzymes such as cytochrome P450 oxidases.

Despite technological advances, not all loci in the human genome can readily be fully genotyped using current conventional methods. Incomplete sequence information, unknown splice junction, unknown size of the deletion, and a large amount of homology with nearby sequence can all contribute to such a problem. In addition, there remains a need for methods and assays to determine susceptibility to and provide diagnosis of autism. Improved methods and additional relevant autism genetic markers are therefore needed.

The citation of references herein shall not be construed as an admission that such is prior art to the present invention.

SUMMARY OF THE INVENTION

The invention relates to the identification and characterization of GSTM1 as a susceptibility gene for autism and autistic disorders. In particular, a GSTM1 deletion, particularly a null deletion mutation, has been found to have a significant association with autism. The presence of GSTM1 null homozygotes is enriched in autism. GSTM1 genotyping, particularly in combination with other genes associated with autism, may be utilized in tests, assays, methods, kits for diagnosing or predicting autism, including disease determination, clinical diagnosis, susceptibility assessment, carrier testing and prenatal diagnosis.

Therefore, the present invention provides methods of identifying an individual as being genetically susceptible to having or developing autism or an autistic disorder. The present invention further provides methods of identifying an individual as being genetically susceptible for having offspring that are susceptible for developing autism or an autistic disorder. Methods of identifying an individual as being susceptible due to genetic or environmental factors for having or developing autism are also provided. The present invention also provides methods of identifying an individual as being susceptible for having or developing an autistic disorder due to both environmental and genetic factors, particularly wherein assessment of the GSTM1 genotype of an individual is made and the result is incorporated in the method.

The present invention therefore provides methods for compiling genetic datasets which include the GSTM1 genotype of an individual or individuals for use in determining a predicted probability for an individual of having a susceptibility for having or developing autism, or for having offspring that develop autism.

The present invention extends to diagnostic assays, kits and methods for determining the GSTM1 genotype of a subject, thereby providing a means to diagnosing or determining susceptibility to autism or autism disorders in a subject.

In accordance with the present invention, a diagnostic assay is provided for determining susceptibility to autism in a subject which comprises
(a) isolating nucleic acid from said subject; and
(b) characterizing the GSTM1 genotype, thereby determining the susceptibility for autism of said subject.

The present invention also provides for the use of the nucleic acids of GSTM1 of the present invention in the methods of the present invention for identifying, diagnosing, preventing and/or treating individuals with autism or a possible or suspected prevalence for autism.

Determining if the biological sample contains the genetic variant of GSTM1, particularly a null mutation, can be performed by any appropriate method including, but not limited to PCR, special PCR, RT PCR, RFLP analysis, SSCP, oligonucleotide hybridization, base extension and FISH. Accordingly, it is a principal object of the present invention to provide a method for identifying an individual that is genetically inclined to develop autism or autistic disease.

It is a further object of the present invention to provide a method for identifying an individual that is genetically inclined to have offspring having autistic disease.

It is a further object of the present invention to provide a method of diagnosing autism.

The invention provides a method for determining the susceptibility of an individual to developing autism comprising:

(a) collecting a biological sample from one or more participants; wherein a participant is either the individual or a blood relative of the individual; and wherein the biological sample contains nucleic acids and/or proteins of the participant;

(b) analyzing the nucleic acids and/or proteins from the biological sample; wherein said analyzing results in a genotype for the gene GSTM1; and wherein said genotype forms a partial or full dataset of genetic explanatory variables for the participants; and (c) analyzing the dataset;

wherein the susceptibility of an individual to develop autism is estimated.

In one aspect of the method, the step c) analyzing utilizes the likelihood ratio test.

In a further aspect of the method, a null mutation of GSTM1 genotype is determined.

In an additional aspect of the method, the genotype for the gene GSTM1 is determined by PCR analysis.

The invention further provides an assay for determining susceptibility to autism in a subject which comprises (a) isolating nucleic acid from said subject; and (b) characterizing the GSTM1 genotype, thereby determining the susceptibility for autism of said subject.

In an embodiment of the assay, the genotype for the gene GSTM1 is determined by PCR analysis.

The invention provides a method of estimating the susceptibility of an individual to have offspring that develop a developmental disorder comprising:

(a) collecting a biological sample from one or more participants; wherein a participant is either the individual or a blood relative of the individual; and wherein the biological sample contains nucleic acids and/or proteins of the participant;

(b) analyzing the nucleic acids and/or proteins from the biological sample; wherein said analyzing results in a genotype for the gene GSTM1; and wherein said genotype forms a partial or full dataset of genetic explanatory variables for the participants; and (e) analyzing the dataset;

wherein the susceptibility of an individual to have offspring that develop autism is estimated.

In an embodiment of this method, the step c) analyzing utilizes the likelihood ratio test.

In a further embodiment of the method, a null mutation of GSTM1 genotype is determined. In a further embodiment, the genotype for the gene GSTM1 is determined by PCR analysis.

The present invention includes a test kit for assessing susceptibility to autism in a subject or in an offspring, comprising nucleic acid probes or primers for determining the GSTM1 genotype of said subject or of said offspring's parents.

Other objects and advantages will become apparent to those skilled in the art from a review of the following description which proceeds with reference to the following illustrative drawings.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the terms shall have the definitions set out below. The terms "glutathione S-transferase M1", "glutathione S-transferase mu", "GST M1", "GST1" and any variants not specifically listed, may be used herein interchangeably, and as used throughout the present application and claims refer to proteins, polypeptides and enzymes, and extends to those nucleic acids encoding said polypeptides, including the upstream and downstream and flanking nucleic acid sequences, including any genetic variants, mutants, and/or null mutants thereof. Accordingly, proteins and nucleic acids displaying substantially equivalent or altered activity or derived from the GSTM1 chromosomal locus are likewise contemplated. These modifications may be deliberate, for example, such as modifications obtained through site-directed mutagenesis, or may be natural variants or accidental, such as those obtained through variations or mutations in mammals including humans or in hosts that are producers of the enzyme. Also, the terms "glutathione S-transferase M1", "glutathione S-transferase mu", "GST M1", "GST1" are intended to include within their scope proteins specifically recited herein as well as all substantially homologous analogs and allelic variations.

Cytosolic and membrane-bound forms of glutathione S-transferase are encoded by two distinct supergene families. Eight distinct classes of the soluble cytoplasmic mammalian glutathione S-transferases have been identified: alpha, kappa, mu, omega, pi, sigma, theta and zeta. The GSTM1 gene encodes a glutathione S-transferase that belongs to the mu class. The mu class of enzymes functions in the detoxification of electrophilic compounds, including carcinogens, therapeutic drugs, environmental toxins and products of oxidative stress, by conjugation with glutathione. The genes encoding the mu class of enzymes are organized in a gene cluster on chromosome 1p13.3 and are known to be highly polymorphic. These genetic variations can change an individual's susceptibility to carcinogens and toxins as well as affect the toxicity and efficacy of certain drugs. Null mutations of this class mu gene have been linked with an increase in a number of cancers, likely due to an increased susceptibility to environmental toxins and carcinogens. Multiple protein isoforms are encoded by transcript variants of this gene. The GSTM1 nucleic acid and protein sequence from humans and various other species are publicly known. Chromosomal region genomic sequences are also public, including flanking nucleic acids, such as the chromosome 1 contig sequence NT_019273. Genbank accessions for the GSTM1 nucleic acid and polypeptide include NM_00561, BC036805 and BC024005.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

An "upstream regulatory region" is a DNA regulatory region capable of binding RNA polymerase in a cell and initiating transcription of a downstream (3' direction) coding sequence. For purposes of defining the present invention, the upstream regulatory region sequence is bounded at its 3' terminus by the transcription initiation site and extends upstream (5' direction) to include the minimum number of bases or elements necessary to initiate transcription at levels detectable above background and under appropriate regulatory control. Within the upstream regulatory region sequence will be found a transcription initiation site (conveniently defined by mapping with nuclease SI), as well as protein binding domains (consensus sequences) responsible for the binding of RNA polymerase and regulatory regions (consensus sequences) responsible for appropriate regulatory control, including cellular expression, induction of expression, etc. Eukaryotic promoters will often, but not always, contain "TATA" boxes and "CAT" or "CATA" boxes.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10 or more nucleotides, preferably 15-25 nucleotides, although it may contain fewer nucleotides or more nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "pg" means picogram, "ng" means nanogram, "ug" or "µg" mean microgram, "mg" means milligram, "ul" or "µl" mean microliter, "ml" means milliliter, "l" means liter.

A labeled oligonucleotide or primer may be utilized in the methods, assays and kits of the present invention. The labeled oligonucleotide may be utilized as a primer in PCR or other method of amplification and may be utilized in analysis, as a reactor or binding partner of the resulting amplified product. In certain methods, where sufficient concentration or sequestration of the GSTM1 nucleic acid has occurred, and wherein the oligonucleotide label and methods utilized are appropriately and sufficiently sensitive, the nucleic acid may be directly analyzed, with the presence of, or presence of a particular label indicative of the result and diagnostic of the GSTM1 genotype. After the labeled oligonucleotide or primer has had an opportunity to react with sites within the sample, the resulting product may be examined by known techniques, which may vary with the nature of the label attached. The label utilized may be radioactive or non-radioactive, including fluorescent, colorimetric or enzymatic. In addition, the label may be, for instance, a physical or antigenic tag which is characterized by its activity or binding.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules can be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

In its broadest aspect, the present invention extends to the utilization of the GSTM1 genotype in diagnostic assays, kits and methods for determining the GSTM1 genotype thereby providing a means to determine the susceptibility to autism in a subject. Diagnostic assays, kits and methods incorporating the determination of the GSTM1 genotype of a subject are provided herein, thereby providing a means to determine the likelihood of or susceptibility to autism in a subject. Methods for determining susceptibility using the likelihood ratio test are also provided.

The genotype of GSTM1 in a subject is particularly relevant in determining likelihood of, assessing susceptibility to, or assisting in clinical diagnosis of autism and autistic disease. Specifically, in evaluating or determining appropriate management or therapy in autism patients, for instance, the determination of GSTM1 genotype, and thereby predicting the expression of GSTM1 in an individual, is relevant and useful. Further, GSTM1 genotype and susceptibility to or likelihood of autism is relevant in carrier testing and prenatal diagnosis. Null GSTM1 homozygosity is enriched in autistic individuals.

The assays and methods of the present invention broadly and generally include and incorporate the following steps in determining the GSTM1 genotype of an individual: (a) isolation of nucleic acid from the individual; (b) amplification of the GSTM1 genomic sequence; and (c) analysis of the GSTM1 genomic sequence.

The step (b) may be performed utilizing any method of amplification, including polymerase chain reaction (PCR), ligase chain reaction (Barany, F. (1991) Proc. Natl. Acad. Sci. 88:189-193), rolling circle amplification (Lizardi, P. M. et al (1998) Nature Genetics 19:225-232), strand displacement amplification (Walker, G. T. et al (1992) Proc. Natl. Acad. Sci. 89:392-396) or alternatively any means or method whereby concentration or sequestration of sufficient amounts of the GSTM1 nucleic acid for analysis may be obtained.

In a further embodiment of this invention, commercial test kits suitable for use by a medical specialist may be prepared to determine GSTM1 genotype, and thereby determine the specific genotype or the presence or absence of GSTM1 in an individual patient.

Accordingly, a test kit may be prepared for determining the GSTM1 genotype of an individual, whereby the GSTM1 genotype is determined, and in a particular embodiment the sequence of GSTM1 is determined. The test kit may include the PCR amplification of the nucleic acid, particularly the genomic region, of GSTM1. In an additional embodiment, the flanking or encoding region of GSTM1 is amplified and its characteristic sequence is determined by assessing susceptibility of the PCR product to cleavage with a particular restriction enzyme or a set of restriction enzymes. In a further embodiment, specific primer sets are utilized in amplification of the nucleic acid region of GSTM1 and the presence or absence of PCR product with the specific primer sets is evaluated in determining the GSTM1 genotype.

The DNA samples from the persons tested may be obtained from any source including blood, a tissue sample, amniotic fluid, a chorionic villus sampling, cerebrospinal fluid, and urine.

GSTM1 has been investigated for susceptibility to various cancers, including acute lymphoblastic leukemia, chronic myelogenous leukemia, gastric cancer, prostate cancer, lung cancer, and colorectal cancer (Aktas D et al (2004) Cancer Genet Cytogenet 154:81-85; Joseph T et al (2004) Pediatr Blood Cancer 43:560-567; Cai I et al (2001) Gastroenterol 7(4):506-9; Garte S et al (2000) Leuk Res 24:971-4; Quinones L (2004) Cancer Lett 174:35-44; Acevedo C et al (2003) The Prostate 57:111-117). GSTM1 genotype has also been assessed for increasing risk of asthma or lung function decline (Imboden M et al (2007) Respir Res 8(1):2). GSTM1 genotype may be determined by any means or methods known in the art, including but not limited to genomic Southern blotting, chromosome analysis, sequencing, RNA analysis, expression analysis, and amplification technologies such as PCR. Multiplex PCR has been used and reported to determine GSTM1 and T1 gene deletion by determining copy number in DNA samples (Moyer A M et al (2007) Clin Cancer Res 13(23):7207-16).

Investigators have utilized the following primers for GSTM1 amplification using multiplex PCR:

```
Forward:
5'-GAACTCCCTGAAAAGCTAAAGC-3'        (SEQ ID NO: 1)

Reverse:
5'-GTTGGGCTCAAATATACGGTGG-3'        (SEQ ID NO: 2)
```

Amplification was performed as follows: initial denaturation at 94° C. 4 minutes, 35 cycles of 1 minute at 94° C., 45 seconds at 55° C., 1 minute at 72° C. and final extension for 10 minutes at 72° C. Null genotype of GSTM1 in this instance is revealed by absence of the 219 bp PCR product for GSTM1 (Canalle R et al (2004) Environ Mol Mutagen 43: 100-109; Taspinar M et al (2008) Swiss Med Wkly 138:12-17).

Imboden et al have utilized the following primers and fluorescently labeled probes for GSTM1:

```
Forward:
5'-GGACATTTTGGAGAACCAGACC-3'        (SEQ ID NO: 3)

Reverse:
5'-CTGGATTGTAGCAGATCATGCC-3'        (SEQ ID NO: 4)

GSTM1-specific probe:
5' VIC-TGGACAACCATATGCAG-MGB 3'     (SEQ ID NO: 5)
```

(Imboden M et al (2007) Respir Res 8(1):2).

In a particular aspect of the invention, the GSTM1 genotype assessment is one component in a multi marker diagnostic test for autism, autistic disorders, or other neurodevelopmental disorders. Assays, methods or kits are contemplated which incorporate additional autism biomarkers or genetic markers, which may collectively with GSTM1 provide information as to susceptibility to or diagnosis of autism.

Autism is a neurodevelopmental syndrome defined by deficits in social reciprocity and communication and by unusual repetitive behaviors. Although an underlying genetic predisposition is well recognized, the etiology of autism is currently unknown. Various markers, mutations, and chromosome deletions have been investigated or reported for association with and relevance for autism disease. Any subset or combination thereof may be combined with or assessed in conjunction with GSTM1 of the present invention in determining susceptibility to, assessing, or diagnosing autism disease or disorders. These include genes which act in conjunction with or in pathways associated with glutathione-S transferase or genes of distinct and unrelated pathways or any combination(s) thereof. The skilled artisan can determine, based on their knowledge of genetic correlation, disease association, statistical assessment etc those genes or other biomarkers which are relevant and significant, particularly and including in combination with GSTM1.

Deletions of various chromosomes, including chromosomes 2, 7, 15, 17, 22 and X have been noted to be associated with autism (Ashley-Koch A et al (1999) Genomics 61:227-236; Casas K A et al (2004) Am J Med Genet 130:331-339; Wassink T H et al (2005) Am J Hum Genet 136:36-44; Fine S E et al (2005) J Atism Dev Disord 35:461-470). Various reviews on genetics of autism set out candidate chromosome deletions, genes, and mutations for correlation with autism disorders or as prevalence or susceptibility markers (Freitag, C M (2007) Molecular Psychiatry 12:2-22; Gillberg C et al (1998) J Autism Dev Disorder 28:415-425; Lauristen M et al (1999) J Child Psychol Pschiatry 40:335-345; Vortsman J A (2006) Molec Psychiatry 11:1-18, 28; Folstein S E (2001) Nat Rev Genet 2:943-955).

Certain neurodevelopmental genes, neurotransporter or neuroreceptor genes have been reported as autism markers. These include reelin, engrailed-2, serotonin inn transporter, neuroligins, (including neuroligins 1, 3, and 4), neurexin 1 beta, GABA receptor gene complex (Ylisaukko-Oja T et al (2005) Eur J Hum Genet 13:1285-1292; Buxbaum J D et al (2002) Mol Psychiatry 7(3):311-316). The more recent increase in prevalence suggests that genetically determined vulnerability to environmental exposure might contribute causatively to autism. Investigators have performed family-based association studies of polymorphisms in genes involved in genes relevant to metabolism of or resistance (or sensitivity) to toxic environmental agents in metal-regulatory transcription factor 1 (MTF1), a multispecific organic anion transporter (ABCC1), proton-coupled divalent metal ion transporters (SLC11A3 and SLC11A2), paraoxonase 1 (PON1), and glutathione S-transferase (GSTP1) genes in autistic disorder families (Serajee F J et al (2004) J Child Neurol 19(6):413-7)

Clock gene anomalies have been suggested as causative factors in autism and may be involved in the etiology of autistic disorder. Problems in sleep, memory and timing are all characteristics of autistic disorder and aspects of sleep, memory and timing are each clock-gene-regulated in other species. Association of Per1 and Npas2 with autism has been reported (Nicholas B et al (2007) Mol Psychiatry 12(6):581-92).

The present invention provides for the use of the nucleic acids, specifically those of GSTM1, of the present invention (as well as other nucleic acids which can be used to identify DNA polymorphisms or deletions and null mutations in the alleles of the GST genes) in the methods of the present invention for identifying, diagnosing, preventing and/or treating individuals.

In methods of estimating the susceptibility due to genetic and/or environmental factors for an individual to have or to develop autism or to have offspring that develop autism, and for the corresponding methods of generating genetic or GSTM1 datasets, the present invention provides a step of analyzing nucleic acids and/or proteins, including GSTM1 from biological samples. In one particular embodiment, the assaying for the presence of the genetic variant of GSTM1 having a nucleotide sequence with a null deletion is included as part of this analysis. This genetic variant of GSTM1 becomes a genetic variable for susceptibility to autism.

The present invention also provides methods of estimating the genetic susceptibility of an individual to have or to develop an autistic disorder and/or for having offspring that develop an autistic disorder. One such embodiment comprises collecting a biological sample from one or more participants. The participant may be either the individual or a blood relative of the individual. The biological sample contains nucleic acids and/or proteins of the participant. The nucleic acids and/or proteins from the biological sample are analyzed resulting in a partial or full genotype for the alleles of the gene GSTM1, optionally including the alleles of other genes involved in or associated with a prevalence or susceptibility to autism. The partial or full genotype forms a dataset of genetic explanatory variables for the participant.

Dietary and epidemiological information for environmental explanatory variables for the participant(s) may also be obtained and used to form a dataset of environmental explanatory variables for the participant(s). The datasets of genetic explanatory variables and the dataset of environmental explanatory variables are added to a genetic and environmental reference dataset forming a combined genetic and environmental dataset. A model may be formulated comprising the genetic and environmental explanatory variables obtained from the participant(s). The combined genetic and environmental dataset is then analyzed and a predicted probability for the individual for having and/or developing autism and/or for having offspring that develop autism is determined. The genetic and environmental susceptibility of an individual to have or to develop autism and/or have offspring that develop autism is estimated. In an embodiment, analyzing the combined genetic and environmental dataset is performed by binary linear regression. In another embodiment the model is modified by adding or subtracting one or more genetic and/or environmental explanatory variables and the combined genetic and environmental dataset is re-analyzed preferably, by binary logistic regression. In this case a model is chosen that best fits the data. This can be accomplished by testing the model for goodness of fit. These methods and models are provided and described in U.S. Pat. Nos. 6,210,950 and 6,912,492, which are incorporated herein by reference in their entirety.

It is further contemplated by the present invention to provide methods that include the testing for a genetic mutations in individual genes associated with glutathione s-transferase, particularly GSTM1, and/or in individual combinations of such genes. In addition, all possible combinatorials, and permutations of such genes including a constellation comprising all of the genes involved in antioxidant enzymes and oxidative stress is envisioned by the present invention. Alternatively, a constellation of genes in which any one or more genes can be excluded from those tested is also contemplated by the present invention. Thus all of such possible constellations are envisioned by, and are therefore part of the present invention.

The present invention also provides for the use of the nucleic acids of GSTM1 of the present invention in the methods of the present invention for identifying, diagnosing, preventing and/or treating individuals with autism or a possible or suspected prevalence for autism.

Determining if the biological sample contains the genetic variant of GSTM1, particularly a null mutation, can be performed by any appropriate method including, but not limited to PCR, special PCR, RT PCR, RFLP analysis, SSCP, oligonucleotide hybridization, base extension and FISH.

In addition, all of the nucleic acids of the present invention including cDNA or genomic DNA can be placed into expression vectors operably associated with an expression control sequence. Alternatively, when the nucleic acid is part of an expression control sequence, the nucleic acid and/or the expression control sequence can be placed into an expression vector to control the expression of a coding sequence, such as a reporter gene. Such expression vectors can then be placed into either eukaryotic or prokaryotic host cells and expressed. The host cells comprising the expression vectors are also part of the present invention. In addition, when the nucleic acid includes a coding sequence or a part of a coding sequence, the present invention includes methods of purifying the gene products from the coding sequence or part thereof, and the purified gene products themselves.

Accordingly, it is a principal object of the present invention to provide a method for identifying an individual that is genetically inclined to develop autism or autistic disease.

It is a further object of the present invention to provide a method for identifying an individual that is genetically inclined to have offspring having autistic disease.

It is a further object of the present invention to provide a method of diagnosing autism.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Autism (autistic disorder) is a pervasive developmental disorder with diagnostic criteria based on abnormal social interactions, language abnormalities, and stereotypes evident prior to 36 months of age [5]. Despite its lack of Mendelian transmission autism is highly genetically determined [6].

The vast majority of cases of autism are unrelated to known teratogens but the phenotypic expression of autism may be affected by the interaction of environmental factors with multiple gene loci. There is evidence supporting a role for oxidative stress in autism [7, 8]. Oxidative stress could interact with common functional polymorphic variants of genes that protect against oxidative stress and could thus affect brain development during gestation or possibly after gestation, contributing to expression of autism. Glutathione (GSH) is the most important endogenous antioxidant due to its ability to bind electrophilic substrates through its free sulfhydryl group [9] and is the most abundant non-protein thiol, occurring in millimolar concentrations in human tissues [10]. Low plasma total GSH (tGSH) levels, elevated levels of oxidized GSH (GSSG) and low ratios of tGSH:GSSG have been reported in autism [11].

Glutathione-S-transferases (GSTs), are an important class of antioxidant enzymes that catalyze conjugation of GSH to toxic electrophiles. GSTs are abundant, accounting for up to 10% of cellular protein [12]. Some genetic polymorphisms of GSTs are known to affect enzyme function. It is possible that a functional GST polymorphism could contribute to the pathogenesis of autism, an effect that could be potentiated by reduced levels of GSH, one of the substrates of GSTs. GSTs are Phase II enzymes that conjugate GSH to activated toxins, xenobiotics and metabolites including products of Phase I enzymes such as cytochrome P450 oxidases.

Despite technological advances, not all loci in the human genome can readily be fully genotyped using current conventional methods. Incomplete sequence information, unknown splice junction, unknown size of the deletion, and a large amount of homology with nearby sequence can all contribute to such a problem.

The GSTM1 locus can be considered a model of such a locus. Heterozygotes involving the GSTM1 deletion, or null, allele cannot be readily detected using standard genotyping methods [1]. In such a case, the investigator can determine genotype only up to homozygous-deletion/not-homozygous-deletion categorization, serving as a reminder that what we label "genotype" in our data analysis is actually an observed phenotype. Studies involving such loci generally use a case-control contigency table analysis with two categories for genotype.

Contemporary research often uses a family-based association study design in examining a number of loci at once. The question naturally arises as to whether case-parent trio DNA be used to advantage over the case-control contigency table analysis at a locus where heterozygotes cannot be reliably distinguished from one of the homozygote genotypes.

This example demonstrates the association of GSTM1 genotype, particularly GSTM1 null mutation, with an increased prevalence of autism. The example also relates to a likelihood ratio test built on possible mating types for a case-parent design. Unlike the well-known transmission disequilibrium test for case-parent trios, the test disclosed here does require allele frequency estimates and so is susceptible to population stratification and admixture effects much as a case control analysis is. The performance of the test in simulations, and in a new dataset involving the GSTM1 deletion allele and the autism phenotype is set forth below.

Polymorphic alleles of GSTs have been reported to contribute to a number of human diseases. We focused on the GSTM1*0 polymorphism because the variant allele is a complete gene deletion that lacks function of the GSTM1 and enzyme. Homozygosity for GSTM1*0 was reportedly associated with an increased risk of prostate cancer in the presence of either the val/val or the ile/val genotypes of the Phase I enzyme CYP1A1 [13]. Homozygosity for GSTM1*0 was associated with increased risk of bladder cancer [14]. GSTM1*0 contributed to risk of hepatocellular cancer in conjunction with environmental factors [15]. GSTM1*0 contributed to breast cancer risk in conjunction with the val/val genotype of the Phase I enzyme, CYP1A1[16]. GSTM1*0 also contributed to the risk of small cell lung cancer [17] and asthma [18].

The cohort (70 nuclear families) was ascertained through the New Jersey Center for Outreach and Services for the Autism Community (COSAC) and the UMDNJ-RWJMS Department of Pediatrics-Division of Neurodevelopmental Disabilities. Each affected individual had diagnosis by the Autism Diagnostic Interview-Revised (ADI-R) and the Autism Diagnostic Observation Schedule-Generic (ADOS-G) [19, 20]. Blood samples were drawn from members of autism families and from unrelated, unaffected controls ascertained from UMDNJ clinics and individuals married into dominant pedigrees of other disorders.

Genotyping of the GSTM1*0 whole gene deletion polymorphism was carried out by the method of Yang et al. [21] with specific primers using a PCR method with the beta-globin gene amplified as a positive control for PCR efficiency.

PCR products were separated on polyacrylamide gels and visualized with ethidium bromide. The GSTM1 product was about 200 bp and the beta-globin product was about 250 bp. In the presence of a positive betaglobin band, the absence of the GSTM band was interpreted as homozygosity for the whole gene deletion allele [21].

The allele frequencies at the GSTM1 are known to vary with the population. For this analysis, the study sample was restricted to the largest racial and ethnic group, namely those self-identifying as Non-Hispanic White. The published homozygous deletion genotype frequency in this population is about 0.5 [22], suggesting a deletion allele frequency q of about 0.7. The final sample reported here consists of 54 complete case-parent trios and 172 controls. Of the cases, 45 were diagnosed with autistic disorder on both the ADI-R and ADOS-G, while 9 were diagnosed with pervasive developmental disorder not otherwise specified on one instrument but autistic disorder on the other.

The observed genotypes are shown in Table 1. The chi-squared test statistics are 4.83 for Pearson's, 3.97 for the 1-df LRT, and 3.98 for the 2-df LRT (based on the previous subsection, the 2-df LRT would not be recommended in this situation, but is included here for completeness), giving p-values of 0.028, 0.046, and 0.137, respectively, with controls included in all tests. The genotype relative risk estimates are $\hat{r}_0=1.85$ for the 1-df test, $\hat{r}_0=1.76$ and $\hat{r}_1=0.94$ for the 2-df test. Estimates of q are 0.73 under model (1) and 0.71 under both models (2) and (3). When controls were not used in the likelihood ratio tests, the chi-squared values were 0.80 and 1.31 for the 1- and 2-df tests, respectively, giving p-values of 0.371 and 0.521. The results for the case-control analysis and the 1-df likelihood ratio test (utilizing controls) are repeated in Table 2.

TABLE 1

Observed genotypes in GSTM1 and autism association study
Observed Genotypes in GSTM1 and Autism Association Study.

| Mating Type | Count |
|---|---|
| Parent-Case Trios: | |
| P P P | 8 |
| P P D | 2 |
| P D P | 6 |
| P D D | 4 |
| D P P | 5 |
| D P D | 8 |
| D D D | 21 |
| Controls: | |
| P | 90 |
| D | 82 |

TABLE 2

Results for GSTM1 and autism association study.

| Method | Pearson | Likelihood Ratio Test |
|---|---|---|
| Chi-square | 4.84 | 3.97 |
| p | 0.028 | 0.046 |
| Effect Size | OR = 2.02 | RR = 1.85 |
| (95% Confidence Interval) | (1.03, 4.04) | (1.07, 3.30) |
| Null allele frequency | 0.69 | 0.71 |

"Pearson" refers to Pearson's chi-square analysis of the case-control data.
"Likelihood Ratio Test" refers to the 1-df test discussed in the text, in this case using the full information in Table 1.
OR = Odds Ratio,
RR = Relative Risk of homozygous deletion genotype relative ($r_1$ in the text).

The full data available, namely case-parent trios along with controls, gives evidence of a heightened risk for autism for GSTM1*0 homozygotes. The population frequency of that genotype is large, but the genotype is presumably interacting with other genetic and environmental risk factors. Absence of the GSTM1 gene in GSTM1*0 homozygotes could lead to failure of individuals with autism to detoxify important compounds, including some that could be agents or products of oxidative stress.

The present findings could be consistent with the hypothesis of a gene-environment interaction that alters the expression of autism because GSTs are detoxification enzymes that conjugate absorbed xenobiotics. These findings could lead to documentation and identification of an exogenous or endogenous moiety interacting with GSTs to contribute to autism and a mechanism of action of select environmental chemicals in contributing to the phenotypic presentation of autism.

As researchers increasingly study larger sets of candidate loci at a time, they will occasionally find that their study design may not be best for a specific locus. While a case-parent design offers many advantages at most loci, it has not generally been considered possible to use such a design to test a locus where the heterozygote cannot be reliably detected. We have demonstrated that, with the risk of the additional assumption of Hardy-Weinberg equilibrium, it is possible to construct such a test. For the same number of genotyped subjects, the resulting test has less power than a Pearson's chi-squared test using cases and controls. If controls can be added, the proposed test has slightly more power, but at a cost of additional genotyping; if that genotyping were instead dedicated to additional controls, the case-control analysis would maintain its superiority in power. The 2-df test appears to be useful only when a recessive model for the deletion allele is suspected, and would require a large sample in that circumstance. The 1-df test, however, is more generally worthwhile when the study participants have already been assembled. It has the advantage that it can be used both when only case-parent information is available as well as when both case-parent and independent control data is available.

With respect to the association study of the GSTM1 locus with autism, both the traditional case-control analysis and the 1-df likelihood ratio test (utilizing controls) support (at $p=0.028$ and $p=0.046$, respectively) the association of the homozygous GSTM1 deletion genotype with an increased risk of autism. There is no evidence that the heterozygous genotype contributes to any increased risk.

Methods

For a given bi-allelic locus, there are 15 possible triplets of genotypes for the father-mother-child trios [2,3]. The left half of Table 3 shows these triplets, expressed in terms of the number of full alleles each trio-member has. The table also shows the population frequency of each triplet under Hardy-Weinberg equilibrium (HWE) in the parents, and the sampling frequencies under the assumptions that each child is a case and that the relative risk of zero copies (one copy) of the full allele for the disorder in question is $r_0$ ($r_1$). The right hand side of the table gives the same information when 2 copies of the full allele cannot be distinguished from 1 copy; 1 or 2 copies are denoted P (for present) and 0 copies are denoted D (for deletion).

TABLE 3

Population and Sampling Frequencies of Case-Parent Trios.

| Actual | | | Observable | | | |
|---|---|---|---|---|---|---|
| F, M, C Genotype | Population Frequency[a] | Case Frequency[b] | F, M, C Genotype | Population Frequency[a] | Case Frequency[b] | Label |
| 2, 2, 2 | $p^4$ | $p^4/M$ | P, P, P | $p^2(3-2p)$ | $p^2(1+2r_1(1-p))/M$ | a |
| 2, 1, 2 | $p^3(1-p)$ | $p^3(1-p)/M$ | | | | |
| 2, 1, 1 | $p^3(1-p)$ | $r_1 p^3(1-p)/M$ | | | | |
| 1, 2, 2 | $p^3(1-p)$ | $p^3(1-p)/M$ | | | | |
| 1, 2, 1 | $p^3(1-p)$ | $r_1 p^3(1-p)/M$ | | | | |
| 1, 1, 2 | $p^2(1-p)^2$ | $p^2(1-p)^2/M$ | | | | |
| 1, 1, 1 | $2p^2(1-p)^2$ | $2r_1 p^2(1-p)^2/M$ | | | | |
| 1, 1, 0 | $p^2(1-p)^2$ | $r_0 p^2(1-p)^2/M$ | P, P, D | $p^2(1-p)^2$ | $r_0 p^2(1-p)^2/M$ | b |
| 2, 0, 1 | $p^2(1-p)^2$ | $r_1 p^2(1-p)^2/M$ | P, D, P | $p(1-p)^2$ | $r_1 p(1-p)^2/M$ | c |
| 1, 0, 1 | $p(1-p)^3$ | $r_1 p(1-p)^3/M$ | | | | |
| 1, 0, 0 | $p(1-p)^3$ | $r_0 p(1-p)^3/M$ | P, D, D | $p(1-p)^3$ | $r_0 p(1-p)^3/M$ | d |
| 0, 2, 1 | $p^2(1-p)^2$ | $r_1 p^2(1-p)^2/M$ | D, P, P | $p(1-p)^2$ | $r_1 p(1-p)^2/M$ | e |
| 0, 1, 1 | $p(1-p)^3$ | $r_1 p(1-p)^3/M$ | | | | |
| 0, 1, 0 | $p(1-p)^3$ | $r_0 p(1-p)^3/M$ | D, P, D | $p(1-p)^3$ | $r_0 p(1-p)^3/M$ | f |
| 0, 0, 0 | $(1-p)^4$ | $r_0(1-p)^4/M$ | D, D, D | $(1-p)^4$ | $r_0(1-p)^4/M$ | g |

"F, M, C" refers to Father, Mother, Child

Note:

$M = p^2(r_0 - 2r_1 + 1) - 2p(r_0 - r_1) + r_0$. The allele frequency of the full allele is denoted by p.

[a]Under the assumption of Hardy-Weinberg equilibrium.

[b]Under the assumption of Hardy-Weinberg equilibrium, and a relative risk of $r_0$ ($r_1$) is the risk for a child with zero copies (one copy) of full allele relative to the risk to a child with two copies of the full allele.

Case-parent trios can be categorized into one of the 7 types on the right of the table. The resulting counts will follow a multinomial distribution. One can then construct a likelihood under a model with 1. $r_1 = r_0 = 1$,
2. $r_1 = 1$ but $r_0$ free, or
3. $r_0$ and $r_1$ free.

The last model might correspond biologically to a dose-response model, while model might correspond to a scientific hypothesis that either one or two copies of the full allele provides the same biological functionality. The likelihood ratio test then has a test statistic equal to twice the difference in the maximized log-likelihoods of the relevant models. Asymptotically that test statistic is distributed as a chi-squared random variable with degrees of freedom equal to the number of additional parameters estimated, namely 1 for the second model versus the first or the third versus the second, and two for the third versus the first. In all models, p, the frequency of the full allele, will be estimated. Data on control subjects, if available, can also be incorporated into the likelihood, yielding more accurate allele frequency estimates.

When just $r_0$ is to be estimated, the maximum likelihood estimator of $r_0$ is simply $$\hat{r}_0 = \frac{n}{m} \frac{1-\hat{q}^2}{\hat{q}^2},$$

where m is the total number of cases with the full allele present, n is the total number of cases homozygous for the null allele, and $\hat{q}$ is the estimated frequency of the null allele. The estimator $\hat{r}_0$ is thus simply the observed ratio of the two detectable genotypes among the cases divided by the ratio expected under the null hypothesis.

When both $r_0$ and $r_1$ are estimated, the maximum likelihood estimators are $$\hat{r}_0 = \frac{n\hat{p}^2}{\hat{q}(a-m\hat{p})}$$

and $$\hat{r} = \frac{(m-a)\hat{p}}{2^1\hat{q}(a-m\hat{p})},$$

with m, n, $\hat{p}$ as before, $\hat{q}=1-\hat{p}$, and a the number of (P,P,P) trios. These estimates do not admit a simple description as when only $r_0$ is estimated.

For all three models, q can be estimated as the solution to a quadratic or cubic equation, although in case ( ) there is a particularly simple form of $\hat{p}=(2b+d+f)/(2n)$, where b, d, and f are as in the mating type table and represent the counts with a non-obligate null homozygous case.

The appendix contains code for the R statistical environment [4] containing functions for the calculating test statistics, estimates, and confidence intervals.

Simulations

To study the power of the likelihood ratio tests compared to the usual case control contingency table analysis, we performed a number of simulations, the results of which are shown in Tables 4 and 5. Each cell in the tables represents 10,000 runs. The simulations vary: the deletion allele frequency q (so the observed homozygous deletion genotype frequency is $q^2$), the relative risks $r_0$ and $r_1$ for zero or one copies of the full allele as compared to the risk for the genotype homozygous for the full allele, and the number of trios (either 50 or 200). For the case control simulations there were twice the number of controls as cases, so that each test involved the same amount of genotyping. The test statistic for the case control simulations was the Pearson chi-squared without continuity correction. Other contingency table test statistics give very similar results (data not shown).

TABLE 4

Power Using Controls in All Tests.

| | | $r_1 = 1$ | | $r_1 = \sqrt{r_0}$ | | $r_1 = r_0$ | |
|---|---|---|---|---|---|---|---|
| q | $r_0$ | LR 1 CC[a] | LR 2 CC[b] | LR 1 CC[a] | LR 2 CC[b] | LR 1 CC[a] | LR 2 CC[b] |
| 50 Case Trios | | | | | | | |
| .25 | 2.0 | 0.24 | 0.20 | 0.13 | 0.13 | 0.07 | 0.11 |
| | | 0.23 | 0.30 | 0.15 | 0.20 | 0.09 | 0.13 |

TABLE 4-continued

Power Using Controls in All Tests.

| | | $r_1 = 1$ | | $r_1 = \sqrt{r_0}$ | | $r_1 = r_0$ | |
|---|---|---|---|---|---|---|---|
| q | $r_0$ | LR 1 CC[a] | LR 2 CC[b] | LR 1 CC[a] | LR 2 CC[b] | LR 1 CC[a] | LR 2 CC[b] |
| .50 | 2.0 | 0.51 | 0.42 | 0.21 | 0.19 | 0.06 | 0.11 |
| | | 0.46 | 0.55 | 0.23 | 0.28 | 0.08 | 0.09 |
| .75 | 2.0 | 0.53 | 0.43 | 0.20 | 0.16 | 0.06 | 0.08 |
| | | 0.48 | 0.54 | 0.19 | 0.22 | 0.06 | 0.06 |
| 200 Case Trios | | | | | | | |
| .25 | 2.0 | 0.69 | 0.60 | 0.35 | 0.33 | 0.11 | 0.27 |
| | | 0.64 | 0.72 | 0.42 | 0.50 | 0.21 | 0.25 |
| .50 | 2.0 | 0.98 | 0.96 | 0.64 | 0.58 | 0.09 | 0.27 |
| | | 0.97 | 0.98 | 0.66 | 0.75 | 0.16 | 0.18 |
| .75 | 2.0 | 0.98 | 0.96 | 0.61 | 0.53 | 0.06 | 0.13 |
| | | 0.97 | 0.99 | 0.59 | 0.66 | 0.07 | 0.07 |

CC[a] = Pearson's Chi-Square with twice as many controls as cases.
CC[b] = Pearson's Chi-Square with four times as many controls as cases.
LR 1 = likelihood ratio test with 1 df, LR 2 = likelihood ratio test with 2 df. Both likelihood tests used twice as many controls as cases.

TABLE 5

Relative Efficiency of Partial Genotyping versus Fully Informative Genotyping.

| | | LR 1 versus TDT | | LR 1 versus Schaid LR$_{Gen}$ | | LR 2 versus | |
|---|---|---|---|---|---|---|---|
| q | $r_0$ | $r_1 = 1$ | $r_1 = \sqrt{r_0}$ | $r_1 = 1$ | $r_1 = \sqrt{r_0}$ | $r_1 = 1$ | $r_1 = \sqrt{r_0}$ |
| .25 | 1.5 | 240 | 24 | 120 | 34 | 70 | 14 |
| | 2.5 | 218 | 27 | 107 | 35 | 98 | 29 |
| .50 | 1.5 | 148 | 44 | 119 | 62 | 90 | 48 |
| | 2.5 | 138 | 51 | 107 | 64 | 93 | 56 |
| .75 | 1.5 | 114 | 76 | 121 | 105 | 94 | 82 |
| | 2.5 | 108 | 77 | 112 | 97 | 95 | 77 |

The table gives the percentage relative efficiency of partial (homozygous deletion versus other) genotyping with the proposed test compared to full genotyping. Numbers less than 100% indicate the proposed test with partial genotyping is less efficient than the standard test with full genotyping.
LR 1 and LR 2 refer to the proposed likelihood ratio tests with 1- and 2-df, respectively.
TDT refers to the transmission-disequilibrium test.
Schaid LR$_{Gen}$ refers to Schaid's 2-df likelihood ratio test [26]. Calculations are based on Table 3.

Controls were not used for the likelihood ratio tests in these tables, but Table 6 shows a selection of results when the controls are used in the likelihood ratio tests.

| | | $r_1 = 1$ | | | $r_1 = \sqrt{r_0}$ | | | $r_1 = r_0$ | | |
|---|---|---|---|---|---|---|---|---|---|---|
| | $r_0$ | CC | LR 1 | LR 2 | CC | LR 1 | LR 2 | CC | LR 1 | LR 2 |
| q = .25 | 1.0 | 0.05 | 0.05 | 0.05 | | | | | | |
| | 1.5 | 0.26 | 0.22 | 0.17 | 0.18 | 0.09 | 0.08 | 0.11 | 0.05 | 0.07 |
| | 2.0 | 0.64 | 0.57 | 0.47 | 0.43 | 0.19 | 0.16 | 0.20 | 0.06 | 0.09 |
| | 2.5 | 0.88 | 0.83 | 0.80 | 0.65 | 0.32 | 0.28 | 0.31 | 0.06 | 0.12 |
| | 3.0 | 0.97 | 0.95 | 0.94 | 0.82 | 0.46 | 0.41 | 0.39 | 0.06 | 0.15 |
| q = .50 | 1.0 | 0.05 | 0.05 | 0.05 | | | | | | |
| | 1.5 | 0.58 | 0.49 | 0.39 | 0.29 | 0.16 | 0.13 | 0.10 | 0.06 | 0.09 |
| | 2.0 | 0.96 | 0.92 | 0.86 | 0.66 | 0.39 | 0.34 | 0.16 | 0.06 | 0.14 |
| | 2.5 | 1.00 | 0.99 | 0.99 | 0.88 | 0.63 | 0.57 | 0.22 | 0.07 | 0.19 |
| | 3.0 | 1.00 | 1.00 | 1.00 | 0.96 | 0.79 | 0.75 | 0.26 | 0.06 | 0.24 |
| q = .75 | 1.0 | 0.05 | 0.05 | 0.05 | | | | | | |
| | 1.5 | 0.62 | 0.51 | 0.41 | 0.25 | 0.17 | 0.14 | 0.06 | 0.06 | 0.07 |
| | 2.0 | 0.97 | 0.92 | 0.86 | 0.59 | 0.41 | 0.35 | 0.07 | 0.06 | 0.11 |
| | 2.5 | 1.00 | 0.99 | 0.98 | 0.81 | 0.63 | 0.55 | 0.08 | 0.06 | 0.12 |
| | 3.0 | 1.00 | 1.00 | 1.00 | 0.92 | 0.79 | 0.71 | 0.09 | 0.06 | 0.15 |

The simulations show that the 1-df likelihood ratio test has somewhat less power than the case control approach under a recessive genetic model ($r_1 = 1$) and much less power under an multiplicative model ($r_1 = \sqrt{r_0}$). None of the tests performed well under a dominant model ($r_1 = r_0$), but with a deletion allele this model seems less likely on biological grounds. It could, however, arise when partial loss of function reduces the gene product below a functional threshold. The 2-df likelihood ratio test was outperformed by the other two tests except under the dominant genetic model. However, under this model none of the tests have much power, so the 2-df test will likely be useful only with very large sample sizes.

Table 6 illustrates that the 1-df likelihood ratio test utilizing the controls data has slightly more power than the contingency table analysis under a recessive model and slightly less power under the multiplicative model. The table shows the case just for $r_0 = 2$, but the pattern holds for other values of $r_0$ (results not shown). Of course the table represents ⅝ as much genotyping for the likelihood ratio tests as for the contingency table analyses. The table also includes the power when the case:control ratio is 1:4, so that the total genotyping is the same as for the likelihood ratio tests. Not surprisingly, this design generally has greatest power except under the dominant genetic model.

TABLE 6

Power with all tests using controls.

|   |   | $r_1 = 1$ | | $r_1 = \sqrt{r_0}$ | | $r_1 = r_0$ | |
|---|---|---|---|---|---|---|---|
| q | $r_0$ | LR 1 $CC^a$ | LR 2 $CC^b$ | LR 1 $CC^a$ | LR 2 $CC^b$ | LR 1 $CC^a$ | LR 2 $CC^b$ |
| 50 Case Trios | | | | | | | |
| .25 | 2.0 | 0.24 | 0.20 | 0.13 | 0.13 | 0.07 | 0.11 |
|     |     | 0.23 | 0.30 | 0.15 | 0.20 | 0.09 | 0.13 |
| .50 | 2.0 | 0.51 | 0.42 | 0.21 | 0.19 | 0.06 | 0.11 |
|     |     | 0.46 | 0.55 | 0.23 | 0.28 | 0.08 | 0.09 |
| .75 | 2.0 | 0.53 | 0.43 | 0.20 | 0.16 | 0.06 | 0.08 |
|     |     | 0.48 | 0.54 | 0.19 | 0.22 | 0.06 | 0.06 |
| 200 Case Trios | | | | | | | |
| .25 | 2.0 | 0.69 | 0.60 | 0.35 | 0.33 | 0.11 | 0.27 |
|     |     | 0.64 | 0.72 | 0.42 | 0.50 | 0.21 | 0.25 |
| .50 | 2.0 | 0.98 | 0.96 | 0.64 | 0.58 | 0.09 | 0.27 |
|     |     | 0.97 | 0.98 | 0.66 | 0.75 | 0.16 | 0.18 |
| .75 | 2.0 | 0.98 | 0.96 | 0.61 | 0.53 | 0.06 | 0.13 |
|     |     | 0.97 | 0.99 | 0.59 | 0.66 | 0.07 | 0.07 |

$CC^a$ = Pearson's Chi-Square with twice as many controls as case.
$CC^b$ = Pearson's Chi-Square with four times as many controls as cases.
LR 1 = likelihood ratio test with 1 df, LR 2 = likelihood ratio test with 2 df. Both likelihood tests use twice as many controls as cases.

REFERENCES

[1] Chen C L, Liu Q, Relling M V: Simultaneous characterization of glutathione S-transferase M1 and T1 polymorphisms by polymerase chain reaction in American whites and blacks. *Pharmacogenetics* 1996, 6(2):187-191.

[2] Schaid D J, Sommer S S: Genotype relative risks: methods for design and analysis of candidate-gene association studies. *Am J Hum Genet* 1993, 53(5):1114-1126.

[3] Weinberg C R, Wilcox A J, Lie R T: A log-linear approach to case-parent-triad data: assessing effects of disease genes that act either directly or through maternal effects and that may be subject to parental imprinting. *Am J Hum Genet* 1998, 62(4):969-978.

[4] R Development Core Team: R: A language and environment for statistical computing. R Foundation for Statistical Computing, Vienna, Austria 2005, [[http://www.R-project.org]]. [ISBN 3-900051-07-0].

[5] Rapin I: Autism. *N Engl J Med* 1997, 337(2):97-104. {24130}

[6] Veenstra-Vanderweele J, Christian S L, Cook E H: Autism as a paradigmatic complex genetic disorder. *Annu Rev Genomics Hum Genet* 2004, 5:379-405, [[http://dx.doi.org/10.1146/annurev-.genom.5.061903.180050]]. {32037}

[7] Söğüt S. Zoroğlu S S, Ozyurt H, Yilmaz H R, Ozuğurlu F, Sivasli E, Yetkin O, Yanik M, Tutkun H, Savas H A, Tarakçioğlu M, Akyol O: Changes in nitric oxide levels and antioxidant enzyme activities may have a role in the pathophysiological mechanisms involved in autism. *Clin Chim Acta* 2003, 331(1-2):111-117. {31461}

[8] Vargas D L, Nascimbene C, Krishnan C, Zimmerman A W, Pardo C A: Neuroglial activation and neuroinflammation in the brain of patients with autism. *Ann Neurol* 2005, 57:67-81, [[http://dx.doi.org/10.1002/ana.20315]]. {31696}

[9] Coles B F, Kadlubar F F: Detoxification of electrophilic compounds by glutathione S-transferase catalysis: determinants of individual response to chemical carcinogens and chemotherapeutic drugs? *Biofactors* 2003, 17(1-4):115-130. {31446}

[10] Li Y, Wei G, Chen J: Glutathione: a review on biotechnological production. *Appl Microbiol Biotechnol* 2004, 66(3):233-242, [[http://dx.doi.org/10.1007/s00253-004-1751-y]]. {31457}

[11] James S J, Cutler P, Melnyk S, Jernigan S, Janak L, Gaylor D W, Neubrander J A: Metabolic biomarkers of increased oxidative stress and impaired methylation capacity in children with autism. *Am J Clin Nutr* 2004, 80(6):1611-1617. {31497}

[12] Parkinson A: Biotransformation of Xenobiotics. In *Casarett & Doull's Toxicology. The Basic Science of Poisons*. Edited by Klaassen C, McGraw-Hill 2001:133-224. {31862}

[13] Hung R J, Boffetta P, Brennan P, Malaveille C, Hautefeuille A, Donato F, Gelatti U, Spaliviero M, Placidi D, Carta A, di Carlo A S, Porru S: GST, NAT, SULT1A1, CYP1B1 genetic polymorphisms, interactions with environmental exposures and bladder cancer risk in a high-risk population. *Int J Cancer* 2004, 110(4):598-604, [[http://dx.doi.org/10.1002/ijc.20157]]. {31753}

[14] Yeh C C, Hsieh L L, Tang R, Chang-Chieh C R, Sung F C: Vegetable/fruit, smoking, glutathione S-transferase polymorphisms and risk for colorectal cancer in Taiwan. *World J Gastroenterol* 2005, 11(10):1473-1480. {31853}

[15] Kirk G D, Turner P C, Gong Y, Lesi O A, Mendy M, Goedert J J, Hall A J, Whittle H, Hainaut P, Montesano R, Wild C P: Hepatocellular carcinoma and polymorphisms in carcinogen-metabolizing and DNA repair enzymes in a population with aflatoxin exposure and hepatitis B virus endemicity. *Cancer Epidemiol Biomarkers Prev* 2005, 14(2):373-379, [[http://dx.doi.org/10.1158/1055-9965.EPI-04-0161]]. {31855}

[16] Chacko P, Joseph T, Mathew B S, Rajan B, Pillai M R: Role of xenobiotic metabolizing gene polymorphisms in breast cancer susceptibility and treatment outcome. *Mutat Res* 2005, 581(1-2):153-163, [[http://dx.doi.org/10.1016/j.mrgentox.2004.11.018]]. {31854}

[17] Alexandrie A K, Nyberg F, Warholm M, Rannug A: Influence of CYP1A1, GSTM1, GSTT1, and NQO1 genotypes and cumulative smoking dose on lung cancer risk in a Swedish population. *Cancer Epidemiol Biomarkers Prev* 2004, 13(6):908-914. {31857}
[18] Tamer L, Calikoğlu M, Ates N A, Yildirim H, Ercan B, Saritas E, Unlu A, Atik U: Glutathione-S-transferase gene polymorphisms (GSTT1, GSTM1, GSTP1) as increased risk factors for asthma. *Respirology* 2004, 9(4):493-498, [[http://dx.doi.org/10.1111/j.1440-1843.2004.00657.x]]. {31857}
[19] Lord C, Rutter M, Couteur A L: Autism Diagnostic Interview-Revised: a revised version of a diagnostic interview for caregivers of individuals with possible pervasive developmental disorders. *J Autism Dev Disord* 1994, 24(5):659-685. {31797}
[20] Lord C, Risi S, Lambrecht L, Cook E H, Leventhal B L, DiLavore P C, Pickles A, Rutter M: The Autism Diagnostic Observation Schedule-Generic: a standard measure of social and communication deficits associated with the spectrum of autism. *J Autism Dev Disord* 2000, 30(3):205-223. {31515}
[21] Yang P, Yokomizo A, Tazelaar H D, Marks R S, Lesnick T G, Miller D L, Sloan J A, Edell E S, Meyer R L, Jett J, Liu W: Genetic determinants of lung cancer short-term survival: the role of glutathione-related genes. *Lung Cancer* 2002, 35(3):221-229. {31487}
[22] Garte S, Gaspari L, Alexandrie A K, Ambrosone C, Autrup H, Autrup J L, Baranova H, Bathum L, Benhamou S, Boffetta P, Bouchardy C, Breskvar K, Brockmoller J, Cascorbi I, Clapper M L, Coutelle C, Daly A, Dell'Omo M, Dolzan V, Dresler C M, Fryer A, Haugen A, Hein D W, Hildesheim A, Hirvonen A, Hsieh L L, Ingelman-Sundberg M, Kalina I, Kang D, Kihara M, Kiyohara C, Kremers P, Lazarus P, Marchand L L, Lechner M C, van Lieshout E M, London S, Manni J J, Maugard C M, Morita S, Nazar-Stewart V, Noda K, Oda Y, Parl F F, Pastorelli R, Persson I, Peters W H, Rannug A, Rebbeck T, Risch A, Roelandt L, Romkes M, Ryberg D, Salagovic J, Schoket B, Seidegard J, Shields P G, Sim E, Sinnet D, Strange R C, Stcker I, Sugimura H, To-Figueras J, Vineis P, Yu M C, Taioli E: Metabolic gene polymorphism frequencies in control populations. *Cancer Epidemiol Biomarkers Prev* 2001, 10(12):1239-1248. {31436}

The complete R code needed for performing the test described in this example, as well as a utility function for counting the case-parent types

```
deletiontrio.test <- function(obs, controls = c(0, 0), cases = c(0, 0),
        prevalence = 0.001){
    if (obs[7] != 0 | length(obs) != 16) stop("Observation vector should
        be of length 16. Observation 7 should be 0
        (Present child of Deletion parents).")
    loglike <- function(p, obs, controls, cases, r0, r1, prevalence){
        qq <- 1 - p
        probs <- c(p^2 * (1 + 2 * r1 * qq),
            r0 * p^2 * qq^2,
            r1 * p    * qq^2,
            r0 * p    * qq^3,
            r1 * p    * qq^2,
            r0 * p    * qq^3,
            0,
            r0 *        qq^4)
        probs <- probs / sum(probs)
        # probs gives the probabilities from Table 1
        allprobs <- c(probs, probs[c(1,2,5,6)] +
            probs[c(3,4,7,8)], probs[c(1,2,3,4)] + probs[c(5,6,7,8)])
        allprobs[7] <- 1 #just avoiding log(0)
        logprobs <- log(allprobs)
```

-continued

```
        baserisk <- prevalence / (r0 * qq^2 + r1 * 2 * p * qq + p^2)
        controlprobs <- c((1 - r0 * baserisk) * qq^2,
            (1 - baserisk) * p^2 + (1 - r1 * baserisk) * 2 * p * qq)
        controlprobs <- controlprobs / sum(controlprobs)
        logcontrolprobs <- log(controlprobs)
        caseprobs <- c(r0 * qq^2, p^2 + r1 * 2 * p * qq)
        caseprobs <- caseprobs / sum(caseprobs)
        logcaseprobs <- log(caseprobs)
        sum(logprobs * obs) + sum(c(logcontrolprobs, logcaseprobs) *
            c(controls, cases))
    }
    # null, one, and two below refer to
    # null: r0 = 1, r1 = 1, one: r0 free, r1 = 1, two: r0 free, r1 free
    minmenull <- function(par, obs, controls, cases, prevalence){
        -loglike(p = par, obs = obs, controls = controls, cases =
cases,
            r0 = 1, r1 = 1, prevalence = prevalence)
    }
    minmeone <- function(par, obs, controls, cases, prevalence){
        -loglike(p = par[1], obs = obs, controls = controls, cases =
cases,
            r0 = par[2], r1 = 1, prevalence = prevalence)
    }
    minmetwo <- function(par, obs, controls, cases, prevalence){
        -loglike(p = par[1], obs = obs, controls = controls, cases =
cases,
            r0 = par[2], r1 = par[3], prevalence = prevalence)
    }
    optimizenull.results <- optimize(f = minmenull,
        interval = c(0 + .0001,1 - .0001), obs = obs, controls =
controls,
        cases = cases, prevalence = prevalence)
    p.null <- optimizenull.results$minimum
    optimizeone.results <- nlminb(start = c(p.null, 1), objective =
minmeone,
        lower = c(.001, .001), upper = c(.999, 1000),
        obs = obs, controls = controls, cases = cases, prevalence =
prevalence)
    if (optimizeone.results$convergence != 0) {
        warning("Model 1:", optimizeone.results$message)
    }
    optimizetwo.results <- nlminb(start = c(optimizeone.results$par,
1),
        objective = minmetwo, lower = c(.001, .001, .001),
        upper = c(.999, 1000, 1000), obs = obs, controls = controls,
        cases = cases, prevalence = prevalence)
    if (optimizetwo.results$convergence != 0) {
        warning("Model 2:", optimizetwo.results$message)
    }
    p.one <- optimizeone.results$par[1]
    p.two <- optimizetwo.results$par[1]
# p is the frequency of the full allele
    r0.one <- optimizeone.results$par[2]
    r0.two <- optimizetwo.results$par[2]
    r1.two <- optimizetwo.results$par[3]
    chi.1v0 <- 2 * (-optimizeone.results$objective +
        optimizenull.results$objective)
    chi.2v0 <- 2 * (-optimizetwo.results$objective +
        optimizenull.results$objective)
    chi.2v1 <- 2 * (-optimizetwo.results$objective +
        optimizeone.results$objective)
# Confidence intervals
    f <- function(r0){-loglike(p = p.one, obs = obs,
        controls = controls, cases = cases, prevalence = prevalence,
        r0 = r0, r1 = 1) -
        optimizeone.results$objective - qchisq(.95, df = 1)/2
    }
    r0.one.lower <- uniroot(f, interval = c(.01, r0.one))$root
    r0.one.upper <- uniroot(f, interval = c(r0.one, 10 * r0.one))$root
    f <- function(r0){-loglike(p = p.two, obs = obs,
        controls = controls, cases = cases, prevalence = prevalence,
        r0 = r0, r1 = r1.two) -
        optimizetwo.results$objective - qchisq(.95, df = 1)/2
    }
    r0.two.lower <- uniroot(f, interval = c(.01, r0.two))$root
    r0.two.upper <- uniroot(f, interval = c(r0.two, 10 * r0.two))$root
    f <- function(r1){-loglike(p = p.two, obs = obs,
        controls = controls, cases = cases, prevalence = prevalence,
        r0 = r0.two, r1 = r1) -
        optimizetwo.results$objective - qchisq(.95, df = 1)/2
```

-continued
```
        }
        r1.two.lower <- uniroot(f, interval = c(.01, r1.two))$root
        r1.two.upper <- uniroot(f, interval = c(r1.two, 10 * r1.two))$root
        r0.one.vec <- c(r0.one, r0.one.lower, r0.one.upper)
        r0.two.vec <- c(r0.two, r0.two.lower, r0.two.upper)
        r1.two.vec <- c(r1.two, r1.two.lower, r1.two.upper)
        names(r0.one.vec) <- names(r0.two.vec) <- names(r1.two.vec) <-
            c("est", "lower CI", "upper CI")
        list(p.null = p.null, p.one = p.one, p.two = p.two,
            r0.one = r0.one.vec,
            r0.two = r0.two.vec,
            r1.two = r1.two.vec,
            chi.1v0 = chi.1v0, chi.2v0 = chi.2v0, chi.2v1 = chi.2v1,
            p.value.1v0 = pchisq(chi.1v0, df = 1, lower.tail = FALSE),
            p.value.2v0 = pchisq(chi.2v0, df = 2, lower.tail = FALSE),
            p.value.2v1 = pchisq(chi.2v1, df = 1, lower.tail = FALSE),
            convergence = c (optimizeone.results$convergence,
                optimizetwo.results$convergence)
        )
}
count.trios <- function(id, father, mother, affected, marker,
    affected.flag = 2, marker.present = 1, marker.absent = 0){
    #
    # counts case-parent trio types
    # individual is considered affected if affected == affected.flag
    # marker is present if marker = marker.present,
    # absent if marker = marker.absent, and missing otherwise
    #
    results <- matrix(0, ncol = 4, nrow = 16)
    results[,1] <- c(1,1,1,1,0,0,0,0,1,1,0,0,9,9,9,9)
    results[,2] <- c(1,1,0,0,1,1,0,0,9,9,9,9,1,1,0,0)
    results[,3] <- c(1,0,1,0,1,0,1,0,1,0,1,0,1,0,1,0)
    newmarker <- rep(NA, length(marker))
    newmarker[marker == marker.present] <- 1
    newmarker[marker == marker.absent] <- 0
    newmarker[is.na(marker)] <- 9
    for (i in 1:length(id)){
        if (is.na(affected[i]) | affected[i] != affected.flag) next
        tempTriplet <- c(newmarker[id == father[i]],
            newmarker[id == mother[i]], newmarker[i])
        temp.matcher <- (results[,1] == tempTriplet[1]) &
            (results[,2] == tempTriplet[2]) &
            (results[,3] == tempTriplet[3])
        results[temp.matcher, 4] <- results[temp.matcher, 4] + 1
    }
    results
}
```

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for determining the susceptibility of an individual to developing autism comprising:
    (a) collecting a biological sample from one or more participants; wherein a participant is either the individual or a blood relative of the individual; and wherein the biological sample contains nucleic acids and/or proteins of the participant;
    (b) determining glutathione S-transferase M1 (GSTM1) genotype in the one or more participants;
wherein said genotype forms a partial or full dataset of genetic explanatory variables for the one or more participants; and
    (c) analyzing the dataset;
    wherein the susceptibility of the individual to develop autism is estimated by determining whether said participant lacks a functional GSTM1 enzyme.

2. The method of claim 1 wherein the step c) analyzing utilizes the likelihood ratio test.

3. The method of claim 1 wherein a null mutation of GSTM1 genotype is determined.

4. The method of claim 1 wherein the genotype for the gene GSTM1 is determined by PCR analysis.

5. An assay for determining the susceptibility to autism in a subject comprising:
    (a) isolating nucleic acid from said subject; and
    (b) characterizing the glutathione S-transferase M1 (GSTM1) genotype, so that the presence or absence of GSTM1 is determined in said subject, thereby determining the susceptibility for autism of said subject by determining whether said subject lacks a functional GSTM1 enzyme.

6. The assay of claim 5 wherein the genotype for the gene GSTM1 is determined by PCR analysis.

7. A method of estimating the susceptibility of an individual to have offspring that develop a developmental disorder comprising:
    (a) collecting a biological sample from one or more participants; wherein a participant is either the individual or a blood relative of the individual; and wherein the biological sample contains nucleic acids and/or proteins of the participant;
    (b) determining the glutathione S-transferase M1 (GSTM1) genotype in one or more participants;
wherein said genotype forms a partial or full dataset of genetic explanatory variables for the one or more participants; and
    (e) analyzing the dataset; wherein the susceptibility of an individual to have offspring that develop autism is estimated by determining whether said participant lacks a functional GSTM1 enzyme.

8. The method of claim 7 wherein the step c) analyzing utilizes the likelihood ratio test.

9. The method of claim 7 wherein a null mutation of GSTM1 genotype is determined.

10. The method of claim 7 wherein the genotype for the gene GSTM1 is determined by PCR analysis.

* * * * *